US005773258A

United States Patent [19]
Birch et al.

[11] Patent Number: 5,773,258
[45] Date of Patent: *Jun. 30, 1998

[54] NUCLEIC ACID AMPLIFICATION USING A REVERSIBLY INACTIVATED THERMOSTABLE ENZYME

[75] Inventors: David Edward Birch, Berkeley; Walter Joseph Laird, Pinole; Michael Anthony Zoccoli, Moraga, all of Calif.

[73] Assignee: Roche Molecular Systems, Inc., Branchburg, N.J.

[*] Notice: The term of this patent shall not extend beyond the expiration date of Pat. No. 5,677,152.

[21] Appl. No.: 680,283

[22] Filed: Jul. 11, 1996

Related U.S. Application Data

[60] Provisional application No. 60/002,673, Aug. 25, 1995.
[51] Int. Cl.$^6$ .............................. C12P 19/34; C12N 9/00; C12N 9/99
[52] U.S. Cl. ..................... 435/91.2; 435/183; 435/184; 435/810
[58] Field of Search ................................. 435/91.2, 810, 435/183, 184

[56] References Cited

U.S. PATENT DOCUMENTS 5,262,525  11/1993  Bonnaffe et al. ........................ 530/411
5,338,671  8/1994  Scalice et al. .......................... 435/91.2

OTHER PUBLICATIONS

Atassi et al. Reaction of Proteins with Citraconic Anhydride, Methods in Enzymology, vol. XXV, pp. 546–553, 1972.
Goldberger and Anfinsen, May, 1962, "The Reversible Masking of Amino Groups in Ribonuclease and Its Possible Usefulness in the Synthesis of the Protein" Biochemistry 1(3):401–405.
Hunter and Ludwig, Sep., 1962, "The Reaction of Imidoesters With Proteins and Related Small Molecules" Imidoesters With Proteins 84:3491–3504.
Habeeb, 1966, "Determination of Free Amino Groups in Proteins by Trinitrobenzenesulfonic Acid" Analytical Biochemistry 14:328–336.
Bailey et al., 1967, "Liver Enzyme Changes in the Developing Rats" Proceedings of the Biochemical Society 103:78p–79p.
Marzotto et al., 1967, "Acetcacetylation of Ribonuclease A" Biochemical and Biophysical Research Communications 26(5):517–521.
Marzotto et al., 1968, "Reversible Acetoacetylation of Amino Groups in Proteins" Biochimica et Biophysica Acta 154:450–456.
Braunitzer et al., Feb., 1968, "Tetrafluorbernsteinsaure–anhydrid, ein neues Reagens zur spezifischen und reversiblen Maskierung der Aminogruppen in Proteinen" Hoppe–Seyler's Z. Physiol. Chem. 349: 265.
Dixon and Perham, 1968, "Reversible Blocking of Amino Groups with Citraconic Anhydride" Biochem. J. 109:312–314.

(List continued on next page.)

Primary Examiner—Kenneth R. Horlick
Assistant Examiner—Joyce Tung
Attorney, Agent, or Firm—George W Johnston; Dennis P. Tramaloni; Douglas A. Petry

[57] ABSTRACT

The present invention provides methods for the amplification of nucleic acids using a reversibly inactivated thermostable enzyme. The reversibly inactivated enzyme is the result of a chemical modification of the protein which inactivates the enzyme. The activity of the inactivated enzyme is recovered by an incubation of the reaction mixture at an elevated temperature prior to, or as part of, the amplification reaction. Non-specific amplification is reduced because the reaction mixture does not support the formation of extension products prior to the activating incubation.

13 Claims, 5 Drawing Sheets

OTHER PUBLICATIONS

Habeeb and Atassi, 1970, "Enzymatic and Immunochemical Properties of Lysozyme—Evaluation of Several Amino Group Reversible Blocking Reagents" Biochemistry 9(25):4939–4944.

Atassi and Habeeb, 1972, "Reaction of Proteins with Citraconic Anhydride" Methods in Enzymology 25(Part B):546–553.

Shetty and Kinsella, 1980, "Ready Separation of Proteins from Nucleoprotein Complexes by Reversible Modifiecation of Lysine Residues" Biochem. J. 191:269–272.

Rozovskaya et al., 1981, "Modification of *Escherichia coli* RNA Polymerase by Diethyl Procarbonate" Molecular biology 15(1):61–66.

Naithani and Gattner, Dec., 1982, "Preparation and Properties of Citraconylinsulins" Hoppe–Seyler's Physiol. Chem. 363:1443–1448.

de la Escalera and Palacian, 1989, "Dimethylmaleic Anhydride, a Specific Reagent for Protein Amino Groups" Biochem. Cell. Biol. 67:63–66.

Nieto and Palacian, 1989, "Effects of Temperature and pH on the Regeneration of the Amino Groups of Ovalbumin After Modification with Citraconic and Dimethylmaleic Anhydrides" Biochimica et Biophysica Acta 749:204–210.

Palacian et al., 1990, Dicarboxylic Acid Anhydrides as Dissociating Agents of Protein–Containing Structures Molecular and Cellular Biochemistry 97:101–111.

Lundblad, R.L., Chemical Reagents for Protein Modification, second edition, Boca Raton, Florida, CRC Press, 1991, Chapter 10, entitled "The Modification of Lysine".

citraconic anhydride   cis-aconitic anhydride

A scheme for the reversible reaction of citraconic anhydride with lysine residues

NUCLEIC ACID AMPLIFICATION USING A REVERSIBLY INACTIVATED THERMOSTABLE ENZYME

This application claims the benefit of U.S. provisional Application No. 60/002,673, filed Aug. 25, 1995.

BACKGROUND OF THE INVENTION

1. Field of the Invention

This invention relates generally to the field of nucleic acid chemistry. More specifically, it relates to methods of amplifying nucleic acid sequences and to methods of reducing non-specific amplification.

2. Description of the Related Art

The polymerase chain reaction (PCR) process for amplifying nucleic acid sequences is well known in the art and disclosed in U.S. Pat. Nos. 4,683,202; 4,683,195; and 4,965,188; each incorporated herein by reference. Commercial vendors, such as Perkin Elmer, Norwalk, Conn., market PCR reagents and publish PCR protocols.

In each cycle of a PCR amplification, a double-stranded target sequence is denatured, primers are annealed to each strand of the denatured target, and the primers are extended by the action of a DNA polymerase. Specificity of amplification depends on the specificity of primer hybridization. Primers are selected to be complementary to, or substantially complementary to, sequences occurring at the 3' end of each strand of the target nucleic acid sequence. Under the elevated temperatures used in a typical PCR, the primers hybridize only to the intended target sequence. However, amplification reaction mixtures are typically assembled at room temperature, well below the temperature needed to insure primer hybridization specificity. Under such less stringent conditions, the primers may bind non-specifically to other only partially complementary nucleic acid sequences (or even to other primers) and initiate the synthesis of undesired extension products, which can be amplified along with the target sequence. Amplification of the non-specific primer extension products can compete with amplification of the desired target sequences and can significantly decrease the efficiency of the amplification of the desired sequence. Problems caused by non-specific amplification are discussed further in Chou et al., 1992, *Nucleic Acids Research* 20(7):1717–1723, incorporated herein by reference.

Non-specific amplification can be reduced by reducing the formation of extension products from primers bound to non-target sequences prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension during the time that the reaction conditions do not insure specific primer hybridization.

Hot-start methods can be carried out manually by opening the reaction tube after the initial high temperature incubation step and adding the missing reagents. However, manual hot-start methods are labor intensive and increase the risk of contamination of the reaction mixture. Hot-start methods which use a heat labile material, such as wax, to separate or sequester reaction components are described in U.S. Pat. No. 5,411,876, incorporated herein by reference, and Chou et al., 1992, supra. In these methods, a high temperature pre-reaction incubation melts the heat labile material, thereby allowing the reagents to mix.

Another method of reducing the formation of extension products from primers bound to non-target sequences prior to the start of the reaction relies on inhibition of the DNA polymerase using a compound which non-covalently binds to the DNA polymerase a heat-reversible manner. U.S. Pat. No. 5,338,671, incorporated herein by reference, describes the use of antibodies specific for a thermostable DNA polymerase to inhibit the DNA polymerase activity. The antibodies must be incubated with the DNA polymerase in a buffer at room temperature prior to the assembly of the reaction mixture in order to allow formation of the antibody-DNA polymerase complex. Antibody inhibition of DNA polymerase activity is inactivated by a high temperature pre-reaction incubation. A disadvantage of this method is that the production of antibodies specific to the DNA polymerase is expensive and time-consuming, especially in large quantities. Furthermore, the addition of antibodies to a reaction mixture may require redesign of the amplification reaction.

The formation of extension products can also be inhibited by the addition of a compound which non-covalently binds to the primers in a heat-reversible manner, thereby preventing the primers from hybridization to any sequence, target or otherwise. For example, single-stranded binding protein added to a reaction mixture will bind the primers, thereby preventing primer hybridization and inhibiting primer extension. Improvements in the yield of PCR products using gene 32 protein are described in Schwarz et al., 1990, *Nucleic Acids Research* 18(4):10, incorporated herein by reference.

Non-specific amplification can be reduced by degrading extension products formed from primers bound to non-target sequences prior to the start of the reaction, such as using the methods described in copending U.S. Ser. No. 07/960,362, now allowed, which is incorporated herein by reference. The degradation of newly-synthesized extension products is achieved by incorporating into the reaction mixture dUTP and UNG, and incubating the reaction mixture at 45°–60° C. prior to carrying out the amplification reaction. A disadvantage of this method is that the degradation of extension product competes with the formation of extension product and the elimination of non-specific primer extension product is likely to be less complete.

Conventional techniques of molecular biology, protein chemistry, and nucleic acid chemistry, which are within the skill of the art, are fully explained fully in the literature. See, for example, Sambrook et al., 1989, *Molecular Cloning—A Laboratory Manual,* Cold Spring Harbor Laboratory, Cold Spring Harbor, N.Y.; *Oligonucleotide Synthesis* (M. J. Gait, ed., 1984); *Nucleic Acid Hybridization* (B. D. Hames and S. J. Higgins. eds., 1984); *Chemical Reagents for Protein Modification* (CRC Press); and a series, *Methods in Enzymology* (Academic Press, Inc.), all of which are incorporated herein by reference. All patents, patent applications, and publications mentioned herein, both supra and infra, are incorporated herein by reference.

SUMMARY OF THE INVENTION

The present invention provides methods and reagents for amplifying nucleic acid using a primer-based amplification reaction which provide a simple and economical solution to the problem of non-specific amplification. The methods use a reversibly inactivated thermostable enzyme which can be reactivated by incubation in the amplification reaction mixture at an elevated temperature. Non-specific amplification is greatly reduced because the reaction mixture does not support primer extension until the temperature of the reaction mixture has been elevated to a temperature which insures primer hybridization specificity.

One aspect of the present invention relates to reversibly inactivated thermostable enzymes which are produced by a reaction between a thermostable enzyme which catalyzes a primer extension reaction and a modifier reagent. The reaction results in a significant, preferably essentially complete, reduction in enzyme activity. Incubation of the modified enzyme in an aqueous buffer at alkaline pH at a temperature which is less than about 25° C. results in essentially no increase in enzyme activity in less than about 20 minutes. Incubation of the modified enzyme in an aqueous buffer, formulated to pH 8–9 at 25° C., at a temperature greater than about 50° C. results in at least a two-fold increase in primer extension activity in less than about 20 minutes. The reversibly inactivated thermostable enzymes of the invention, in their active state, either catalyze primer extension or are necessary for primer extension to occur. Preferred enzymes include thermostable DNA polymerases and ligases.

Preferred modifier reagents are dicarboxylic acid anhydrides of the general formula:

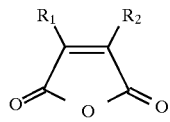

where $R_1$ and $R_2$ are hydrogen or organic radicals, which may be linked, or of the general formula:

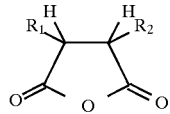

where $R_1$ and $R_2$ are organic radicals, which may be linked, and the hydrogen are cis. The organic radical may be directly attached to the ring by a carbon-carbon bond or through a carbon-hereoatom bond, such as a carbon-oxygen, carbon-nitrogen, or carbon-sulphur bond. The organic radicals may also be linked to each other to form a ring structure as in, for example, 3,4,5,6-tetrahydrophthalic anhydride.

Preferred reagents include maleic anhydride; substituted maleic anhydrides such as citraconic anhydride, cis-aconitic anhydride, and 2,3-dimethylmaleic anhydride; exo-cis-3,6-endoxo-$\Delta^4$-tetrahydropthalic anhydride; and 3,4,5,6-tetrahydrophthalic anhydride. In particular, citraconic anhydride and cis-aconitic anhydride are preferred for the preparation of reversibly inactivated DNA polymerases for use in PCR amplifications.

Another aspect of the present invention relates to methods for carrying out a nucleic acid amplification reaction using a reversibly-inactivated thermostable enzyme of the present invention. The present invention provides methods for the amplification of a target nucleic acid contained in a sample comprising the steps of:

(a) contacting the sample with an amplification reaction mixture containing a primer complementary to the target nucleic acid and a modified thermostable enzyme, wherein the modified thermostable enzyme is produced by a reaction of a mixture of a thermostable enzyme which catalyzes a primer extension reaction and a modifier reagent, wherein the reaction is carried out at alkaline pH at a temperature which is less than about 25° C., wherein the reaction results in a chemical modification of the enzyme which results in essentially complete inactivation of enzyme activity, and wherein incubation of the modified enzyme in an aqueous buffer, formulated to pH 8–9 at 25° C., at a temperature greater than about 50° C. results in at least a two-fold increase in enzyme activity in less than about 20 minutes; and (b) incubating the resulting mixture of step (a) at a temperature which is greater than about 50° C. for a time sufficient to reactivate the enzyme and allow formation of primer extension products.

As a preferred method, the present invention provides a method for the amplification of a target nucleic acid contained in a sample, comprising:

(a) contacting the sample with an amplification reaction mixture containing a primer complementary to the target nucleic acid and a modified thermostable enzyme, wherein the modified thermostable enzyme is produced by a reaction of a mixture of a thermostable enzyme and a dicarboxylic acid anhydride of the general formula:

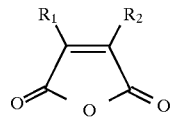

where $R_1$ and $R_2$ are hydrogen or organic radicals, which may be linked, or of the general formula:

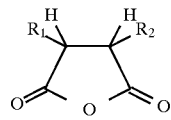

where $R_1$ and $R_2$ are organic radicals, which may be linked, and the hydrogen are cis, wherein the reaction results in essentially complete inactivation of enzyme activity; and (b) incubating the resulting mixture of step (a) at a temperature which is greater than about 50° C. for a time sufficient to reactivate the enzyme and allow formation of primer extension products.

Preferred embodiments of the methods use reversibly modified enzymes modified using the preferred modifier reagents. In some embodiments of the invention, the incubation step, step (b), is carried out prior to the start of the amplification reaction. In other embodiments, the incubation which results in reactivation of the enzyme is an integral step in the amplification process. For example, the denaturation step carried out in each PCR cycle can function simultaneously to reactivate a modified DNA polymerase.

In a preferred embodiment of the invention, the amplification reaction is a polymerase chain reaction (PCR) and a reversibly-inactivated thermostable DNA polymerase is used. The reaction mixture is incubated prior to carrying out the amplification reaction at a temperature which is higher than the annealing temperature of the amplification reaction. Thus, the DNA polymerase is inactivated until the temperature is above the temperature which insures specificity of the amplification reaction, thereby reducing non-specific amplification.

Another aspect of the invention relates to amplification reaction mixtures which contain a reversibly-inactivated thermostable enzyme of the present invention along with reagents for carrying out the amplification reaction. In a preferred embodiment, the amplification reaction mixture contains oligonucleotide primers for carrying out a PCR.

Another aspect of the invention relates to kits which comprise a reversibly inactivated thermostable enzyme of the invention and one or more amplification reagents.

DESCRIPTION OF THE PREFERRED EMBODIMENTS

Figure 1:
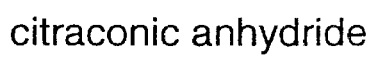
FIG. 1 shows the structures of citraconic anhydride, cis-aconitic anhydride, and 2,3-dimethylmaleic anhydride, and the reaction between citraconic anhydride and lysine.
Figure 1:
Figure 1:
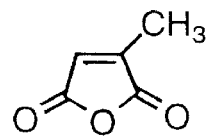
Figure 1:
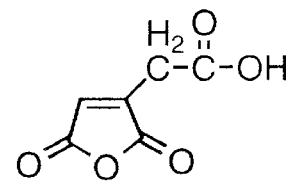
Figure 1:
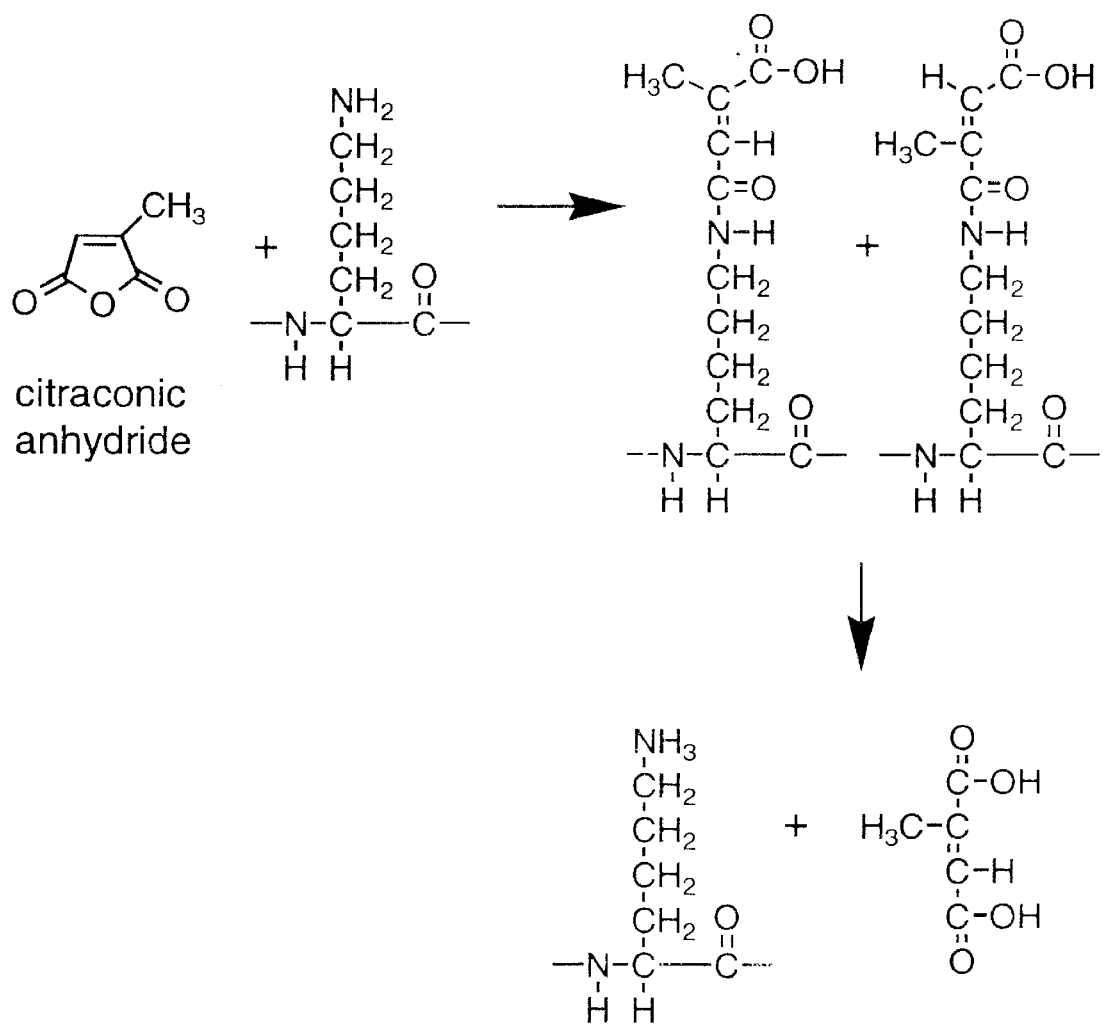

To aid in understanding the invention, several terms are defined below.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA. Oligonucleotide can be prepared by any suitable method. A review of synthesis methods is provided in Goodchild, 1990, *Bioconjugate Chemistry* 1(3):165–187, incorporated herein by reference.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1989, supra).

Generally, stringent hybridization conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridization conditions will allow sequence mismatches to be tolerated; the degree of mismatch tolerated can be controlled by suitable adjustment of the hybridization conditions.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. Oligonucleotide analogues, such as "peptide nucleic acids", can act as primers and are encompassed within the meaning of the term "primer" as used herein. A primer is preferably a single-stranded oligodeoxyribonucleotide. The appropriate length of a primer depends on the intended use of the primer but typically ranges from 6 to 50 nucleotides. Short primer molecules generally require cooler temperatures to form sufficiently stable hybrid complexes with the template. A primer need not reflect the exact sequence of the template nucleic acid, but must be sufficiently complementary to hybridize with the template.

The term "primer extension" as used herein refers to both to the synthesis of DNA resulting from the polymerization of individual nucleoside triphosphates using a primer as a point of initiation, and to the joining of additional oligonucleotides to the primer to extend the primer. As used herein, the term "primer extension" is intended to encompass the ligation of two oligonucleotides to form a longer product which can then serve as a target in future amplification cycles. As used herein, the term "primer" is intended to encompass the oligonucleotides used in ligation-mediated amplification processes which are extended by the ligation of a second oligonucleotide which hybridizes at an adjacent position.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

The terms "target region" and "target nucleic acid" refers to a region or subsequence of a nucleic acid which is to be amplified. The primer hybridization site can be referred to as the target region for primer hybridization.

As used herein, an oligonucleotide primer is "specific" for a target sequence if the number of mismatches present between the oligonucleotide and the target sequence is less than the number of mismatches present between the oligonucleotide and non-target sequences which may be present in the sample. Hybridization conditions can be chosen under which stable duplexes are formed only if the number of mismatches present is no more than the number of mismatches present between the oligonucleotide and the target sequence. Under such conditions, the oligonucleotide can form a stable duplex only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

The term "non-specific amplification" refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization", and can occur during the lower temperature, reduced stringency pre-reaction conditions.

The term "thermostable enzyme" refers to an enzyme that is relatively stable to heat. The thermostable enzymes can withstand the high temperature incubation used to remove the modifier groups, typically greater than 50° C., without suffering an irreversible loss of activity. Modified thermostable enzymes usable in the methods of the present invention include thermostable DNA polymerases and thermostable ligases.

The term "thermostable DNA polymerase" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. Purified thermostable DNA polymerases are described in U.S. Pat. No. 4,889,818; U.S. Pat. No. 5,352,600; U.S. Pat. No. 5,079,352; PCT/US90/07639; PCT/US91/05753; PCT/US91/0703; PCT/US91/07076; co-pending U.S. patent application Ser. No. 08/062,368; WO 92/09689; and U.S. Pat. No. 5,210,036; each incorporated herein by reference.

An enzyme "derived" from an organism herein refers to an enzyme which is purified from the organism or a recombinant version of an enzyme which is purified from the organism, and includes enzymes in which the amino acid sequence has been modified using techniques of molecular biology.

The term "reversibly inactivated", as used herein, refers to an enzyme which has been inactivated by reaction with a compound which results in the covalent modification (also referred to as chemically modification) of the enzyme, wherein the modifier compound is removable under appropriate conditions. The reaction which results in the removal of the modifier compound need not be the reverse of the modification reaction. As long as there is a reaction which results in removal of the modifier compound and restoration of enzyme function, the enzyme is considered to be reversibly inactivated.

The term "reaction mixture" refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a thermostable DNA polymerase, dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, and to allow for independent adjustment of the concentrations of the components depending on the application, and, furthermore, that reaction components are combined prior to the reaction to create a complete reaction mixture.

The methods of the present invention involve carrying out an amplification reaction using a heat-activated thermostable enzyme, wherein the active enzyme is required for primer extension. Prior to the high temperature incubation which activates the enzyme, the amplification reaction mixture does not support primer extension and no extension products, non-specific or otherwise, are formed. Following the high temperature incubation which reactivates the enzyme, the amplification reaction is maintained at elevated temperatures which insure reaction specificity. Thus, primer extension products are formed only under conditions which insure amplification specificity.

In the methods of the present invention, the heat-activated enzyme, in its active state, catalyzes the primer extension reaction. For use in a typical amplification reaction, e.g., a PCR, the heat-activated thermostable enzyme possesses, in its active state, DNA polymerase activity. For use in ligase-mediated amplification systems, the heat-activated thermostable enzyme possesses, in its active state, DNA ligase activity.

In a ligase-meditated amplification system, an "extension product" is formed by the ligation of a first oligonucleotide (herein encompassed by the term "primer") to a second oligonucleotide which hybridizes adjacent to the 3' end of the first oligonucleotide. The second oligonucleotide may be hybridized immediately adjacent to the primer, in which case only ligation is required, or may be hybridized one or more bases away from the primer, in which case polymerase activity is required to extend the primer prior to ligation. In either case, the joining of two oligonucleotides which hybridize to adjacent regions of the target DNA is intended to be herein encompassed by the term "primer extension".

Reversibly Inactivated Thermostable Enzymes

The reversibly inactivated thermostable enzymes of the invention are produced by a reaction between the enzyme and a modifier reagent, which results in a reversible chemical modification of the enzyme, which results in the loss of all, or nearly all, of the enzyme activity. The modification consists of the covalent attachment of the modifier group to the protein. The modifier compound is chosen such that the modification is reversed by incubation at an elevated temperature in the amplification reaction buffer. Suitable enzymes and modifier groups are described below.

Enzymes

Reversibly inactivated enzymes which possess, in their active states, DNA polymerase activity are prepared from thermostable DNA polymerases. Thermostable DNA polymerase usable in amplification reactions are well known in the art and can be derived from a number of sources, such as thermophilic eubacteria or archaebacteria from species of the genera Thermus, Thermotoga, Thermococcus, Pyrodictium, Pyrococcus, and Thermosipho. Representative species from which thermostable DNA polymerases useful in PCR amplifications have been derived include *Thermus aquaticus, Thermus thermophilus, Thermotoga maritima, Pyrodictium occultum, Pyrodictium abyssi,* and *Thermosipho africanus.* Thermostable DNA polymerases are described in U.S. Pat. No. 4,889,818; U.S. Pat. No. 5,352,600; U.S. Pat. No. 5,079,352; PCT/US90/07639; PCT/US91/05753; PCT/US91/0703; PCT/US91/07076; copending U.S. Ser. No. 08/062,368; WO 92/09689; and U.S. Pat. No. 5,210,036; each incorporated herein by reference. Thermostable DNA polymerases are available commercially from Perkin Elmer, Norwalk, Conn.

Reversibly inactivated thermostable enzymes suitable for use in other amplification processes, such as ligase-mediated amplifications, are prepared from the thermostable enzymes described in the references cited below which describe the various amplification methods.

The methods of the present invention are not limited to the use of the exemplified enzymes. For example, any thermostable DNA polymerase described in the literature for use in amplification reactions can be modified as described herein to produce a reversibly inactivated enzyme suitable for use in the present methods. In general, any enzyme which catalyzes primer extension, or is required for primer extension to occur, and is sufficiently thermostable to withstand a high-temperature reactivation incubation without becoming irreversibly inactivated, and can be modified as described herein to produce a reversibly inactivated enzyme, can be used in the present methods. One of skill in the art will be able to optimize the modification reaction and amplification reaction conditions for any given enzyme based on the guidance herein.

Modifier Reagents

In preferred embodiments of the invention, reversible inactivation of a thermostable enzyme is carried out by reversible blocking of lysine residues by chemical modification of the $\epsilon$-amino group of the lysine residues. Modification of the lysines in the active region of the protein results in inactivation of the protein. Additionally, modification of lysines outside the active region may contribute to the inactivation of the protein through steric interaction or conformational changes. A number of compounds have been described in the literature which react with amino groups in a reversible manner. For example, amino groups have been reversibly modified by trifluoroacetylation (see Goldberger and Anfinsen, 1962, Biochemistry 1:410), amidination (see Hunter and Ludwig, 1962, J. Amer. Chem. Soc. 84:3491), maleylation (see Butler et al., 1967, Biochem. J. 103:78), acetoacetylation (see Marzotto et al., 1967, Biochem. Biophys. Res. Commun. 26:517; and Marzotto et al., 1968, Biochim. Biophys. Acta 154:450), tetrafluorosuccinylation (see Braunitzer et al., 1968, Hoppe-Seyler's Z. Physiol. Chem. 349:265), and citraconylation (see Dixon and Perham, 1968, Biochem. J. 109:312–314; and Habeeb and Atassi, 1970, Biochemistry 9(25):4939–4944). All of the above references are incorporated herein by reference.

Preferred reagents for the chemical modification of the $\epsilon$-amino group of lysine residues are dicarboxylic acid anhydrides, of the general formula:

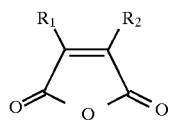

where $R_1$ and $R_2$ are hydrogen or organic radicals, which may be linked, or of the general formula:

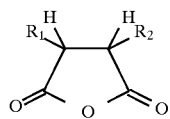

where $R_1$ and $R_2$ are organic radicals, which may be linked, and the hydrogen are cis. The organic radical may be directly attached to the ring by a carbon-carbon bond or through a carbon-hereoatom bond, such as a carbon-oxygen, carbon-nitrogen, or carbon-sulphur bond. The organic radicals may also be linked to each other to form a ring structure as in, for example, 3,4,5,6-tetrahydrophthalic anhydride.

Dicarboxylic acid anhydrides react with the amino groups of proteins to give the corresponding acylated products, as shown for citraconic anhydride in FIG. 1. The reversibility of the above dicarboxylic acid anhydrides is believed to be enhanced by the presence of either the cis-carbon-carbon double bond or the cis hydrogens, which maintains the terminal carboxyl group of the acylated residues in a spatial orientation suitable for interaction with the amide group, and subsequent deacylation. See Palacian et al., 1990, Mol. Cell. Biochem. 97:101–111, incorporated herein by reference, for descriptions of plausible mechanisms for both the acylation and deacylation reactions. Other substituents may similarly limit rotation about the 2,3 bond of the acyl moiety in the acylated product, and such compounds are expected to function in the methods of the present invention.

Examples of the preferred reagents include maleic anhydride; substituted maleic anhydrides such as citraconic anhydride, cis-aconitic anhydride, and 2,3-dimethylmaleic anhydride; exo-cis-3,6-endoxo-$\Delta^4$-tetrahydropthalic anhydride; and 3,4,5,6-tetrahydrophthalic anhydride. The reagents are commercially available from, for example, Aldrich Chemical Co. (Milwaukee, Wis.), Sigma Chemical Co. (St. Louis, Mo.), or Spectrum Chemical Mfg. Corp. (Gardena, Calif.). Modifications of thermostable DNA polymerases using the substituted maleic anhydride reagents citraconic anhydride and cis-aconitic anhydride are described in the Examples.

The relative stabilities of the amino groups acylated using the above reagents decreases in the following order: maleic anhydride; exo-cis-3,6-endoxo-$\Delta^4$-tetrahydropthalic anhydride; citraconic anhydride; 3,4,5,6-tetrahydrophthalic anhydride; cis-aconitic anhydride; and 2,3-dimethylmaleic anhydride (see Palacian et al., supra). Optimal activation incubation conditions for enzymes modified with a particular reagent are determined empirically as described in the Examples.

U.S. Pat. No. 5,262,525, incorporated herein by reference, describes methods for the chemical modification of proteins which use compounds which are dicarboxylic acid anhydrides prepared by Diels-Alder reaction of maleic anhydride and a diene. Compounds described in the '525 patent which have the stability specified herein may be suitable in the present invention.

The methods of the present invention are not limited to the exemplified modifier compounds or to the modification of the protein by chemical modification of lysine residues. Any of the compounds described in the literature which react with proteins to cause the reversible loss of all, or nearly all, of the enzyme activity, wherein the modification is reversible by incubation at an elevated temperature in the amplification reaction buffer, is suitable for preparation of a reversibly inactivated enzyme. As new compounds which reversibly modify proteins become available, these too will be suitable for use in the present methods. Thus, compounds for the preparation of the modified thermostable enzymes of the present invention include compounds which satisfy the following properties:

(1) reaction with a thermostable enzyme which catalyzes primer extension results in a significant inactivation of the enzyme;

(2) incubation of the resulting modified enzyme in an aqueous buffer at about pH 8–9 at a temperature at or below about room temperature (25° C.) results in no significant increase in enzyme activity in less than about 20 minutes; and (3) incubation of the resulting modified thermostable enzyme in an amplification reaction buffer, formulated to about pH 8–9 at room temperature, at an elevated temperature greater than about 50° C. results in at least a two-fold increase in enzyme activity in less than about 20 minutes.

The suitability of a particular modifier compound can be empirically determined routinely following the guidance provided herein. Experimental procedures for measuring the above properties, the degree of attenuation of enzyme activity resulting from modification of the protein and the degree of recovery of enzyme activity following incubation at elevated temperatures in an amplification reaction mixture, are described in the Examples.

Preparation of the Reversibly Inactivated Thermostable Enzymes

The chemical modification of lysine residues in proteins is based on the ability of the ϵ-amino group of this residue to react as a nucleophile. The unprotonated amino group is the reactive form, which is favored at alkaline pH. The modification reaction is carried out at pH 8.0 to 9.0 in an aqueous buffer at a temperature at or below room temperature (25° C.). The reaction is essentially complete following an incubation for 12–24 hours. Suitable reaction conditions are known in the art and are described further in the examples.

Dicarboxylic acid anhydrides react easily with water to give the corresponding acids. Therefore, a large fraction of the reagent is hydrolyzed during modification of the protein amino groups. The rate of hydrolysis increases with pH. The increase in hydrolysis which occurs at pH greater than about 9 can result in suboptimal acylation of the protein.

In general, a molar excess of the modifier reagent relative to the protein is used in the acylation reaction. The optimal molar ratio of modifier reagent to enzyme depends on the reagent used and is determined empirically. As an example, Taq DNA polymerase is essentially completely inactivated (<5% of original activity) by a reaction with a 20-fold or greater molar excess of citraconic anhydride. The minimum molar ratio of modifier which results in essentially complete inactivation of the enzyme can be determined by carrying out inactivation reactions with a dilution series of modifier reagent, as described in the examples.

In the methods of the present invention, it is not necessary that the enzyme be completely inactivated, only that the enzyme be significantly inactivated. As used herein, an enzyme is significantly inactivated if the activity of the enzyme following reaction with the modifier is less than about 50% of the original activity. A reduction in non-specific amplification can be obtained using a significantly inactivated enzyme. A molar ratio of modifier to enzyme in the reaction can be empirically selected that will result in either essentially complete inactivation or significant inactivation of the enzyme following the guidance provided herein. Suitable molar ratios are provided in the Examples. Suitable reaction conditions for the inactivation of enzymes not exemplified can be determined by routine experimentation following the guidance provided herein.

An important aspect of the heat-inactivated enzymes of the present invention is their storage stability. In general, the compounds described herein are stable for extended periods of time, which eliminates the need for preparation immediately prior to each use. For example, citraconylated Taq DNA polymerase was found to remain inactivated for at least four weeks when stored at 25° C. Recommended storage conditions vary depending on which modifier is used, but in general a preparation of inactivated enzyme should be stored at or below room temperature (25° C.), preferably refrigerated. In particular, more unstable modified enzymes, such as those modified with 2,3 dimethylmaleic anhydride, should be stored refrigerated.

Amplification Methods

The methods of the present invention involve the use of a reaction mixture containing a reversibly inactivated thermostable enzyme and subjecting the reaction mixture to a high temperature incubation prior to, or as an integral part of, the amplification reaction. The high temperature incubation results in deacylation of the amino groups and recovery of enzyme activity.

The deacylation of the modified amino groups results from both the increase in temperature and a concomitant decrease in pH. Amplification reactions typically are carried out in a Tris-HCl buffer formulated to a pH of 8.0 to 9.0 at room temperature. At room temperature, the alkaline reaction buffer conditions favor the acylated form of the amino group. Although the pH of the reaction buffer is adjusted to a pH of 8.0 to 9.0 at room temperature, the pH of a Tris-HCl reaction buffer decreases with increasing temperature. Thus, the pH of the reaction buffer is decreased at the elevated temperatures at which the amplification is carried out and, in particular, at which the activating incubation is carried out. The decrease in pH of the reaction buffer favors deacylation of the amino groups.

The change in pH which occurs resulting from the high temperature reaction conditions depends on the buffer used. The temperature dependence of pH for various buffers used in biological reactions is reported in Good et al., 1966, *Biochemistry* 5(2):467–477, incorporated herein by reference. For Tris buffers, the change in pKa, i.e., the pH at the midpoint of the buffering range, is related to the temperature as follows: $\Delta pKa/°C.=-0.031$. For example, a Tris-HCl buffer assembled at 25° C. undergoes a drop in pKa of 2.17 when raised to 95° C. for the activating incubation.

Although amplification reactions are typically carried out in a Tris-HCl buffer, amplification reactions may be carried out in buffers which exhibit a smaller or greater change of pH with temperature. Depending on the buffer used, a more or less stable modified enzyme may be desirable. For example, using a modifying reagent which results in a less stable modified enzyme allows for recovery of sufficient enzyme activity under smaller changes of buffer pH. An empirical comparison of the relative stabilities of enzymes modified with various reagents, as provided above, guides selection of a modified enzyme suitable for use in particular buffers.

In the methods of the present invention, activation of the modified enzyme is achieved by an incubation carried out at a temperature which is equal to or higher than the primer hybridization (annealing) temperature used in the amplification reaction to insure amplification specificity. The length of incubation required to recover enzyme activity depends on the temperature and pH of the reaction mixture and on the stability of the acylated amino groups of the enzyme, which depends on the modifier reagent used in the preparation of the modified enzyme. A wide range of incubation conditions are usable; optimal conditions are determined empirically for each reaction. In general, an incubation is carried out in the amplification reaction buffer at a temperature greater than about 50° C. for between about 10 seconds and about 20 minutes. Optimization of incubation conditions for the reactivation of enzymes not exemplified, or for reaction mixtures not exemplified, can be determined by routine experimentation following the guidance provided herein.

In a preferred embodiment, a PCR amplification is carried out using a reversibly inactivated thermostable DNA polymerase. The annealing temperature used in a PCR amplification typically is about 55°–75° C., and the pre-reaction incubation is carried out at a temperature equal to or higher than the annealing temperature, preferably a temperature greater than about 90° C. The amplification reaction mixture preferably is incubated at about 90°–100° C. for up to about 12 minutes to reactivate the DNA polymerase prior to the temperature cycling. Suitable pre-reaction incubation conditions for typical PCR amplifications are described in the Examples, along with the effect on amplification of varying the pre-reaction incubation conditions.

The first step in a typical PCR amplification consists of heat denaturation of the double-stranded target nucleic acid. The exact conditions required for denaturation of the sample nucleic acid depends on the length and composition of the sample nucleic acid. Typically, an incubation at 90°–100° C. for about 10 seconds up to about 4 minutes is effective to fully denature the sample nucleic acid. The initial denaturation step can serve as the pre-reaction incubation to reactivate the DNA polymerase. However, depending on the length and temperature of the initial denaturation step, and on the modifier used to inactivate the DNA polymerase, recovery of the DNA polymerase activity may be incomplete. If maximal recovery of enzyme activity is desired, the pre-reaction incubation may be extended or, alternatively, the number of amplification cycles can be increased.

In a preferred embodiment of the invention, the modified enzyme and initial denaturation conditions are chosen such that only a fraction of the recoverable enzyme activity is recovered during the initial incubation step. Subsequent cycles of a PCR, which each involve a high-temperature denaturation step, result in further recovery of the enzyme activity. Thus, activation of enzyme activity is delayed over the initial cycling of the amplification. This "time release" of DNA polymerase activity has been observed to further decrease non-specific amplification. It is known that an excess of DNA polymerase contributes to non-specific amplification. In the present methods, the amount of DNA polymerase activity present is low during the initial stages of the amplification when the number of target sequences is low, which reduces the amount of non-specific extension products formed. Maximal DNA polymerase activity is present during the later stages of the amplification when the number of target sequences is high, and which enables high amplification yields. If necessary, the number of amplification cycles can be increased to compensate for the lower amount of DNA polymerase activity present in the initial cycles. The effect on amplification of varying the amplification cycle number is shown in the Examples.

An advantage of the methods of the present invention is that the methods require no manipulation of the reaction mixture following the initial preparation of the reaction mixture. Thus, the methods are ideal for use in automated amplification systems and with in-situ amplification methods, wherein the addition of reagents after the initial denaturation step or the use of wax barriers is inconvenient or impractical.

The methods of the present invention are particularly suitable for the reduction of non-specific amplification in a PCR. However, the invention is not restricted to any particular amplification system. The reversibly-inactivated enzymes of the present invention can be used in any primer-based amplification system which uses thermostable enzymes and relies on reaction temperature to achieve amplification specificity. The present methods can be applied to isothermal amplification systems which use thermostable enzymes. Only a transient incubation at an elevated temperature is required to recover enzyme activity. After the reaction mixture is subjected to a high temperature incubation in order to recover enzyme activity, the reaction is carried out at an appropriate reaction temperature.

Other amplification methods in addition to the PCR (U.S. Pat. Nos. 4,683,195; 4,683,202; and 4,965,188) include, but are not limited to, the following: Ligase Chain Reaction (LCR, Wu and Wallace, 1989, *Genomics* 4:560–569 and Barany, 1991, *Proc. Natl. Acad. Sci. USA* 88:189–193); Polymerase Ligase Chain Reaction (Barany, 1991, *PCR Methods and Applic.* 1:5–16); Gap-LCR (PCT Patent Publication No. WO 90/01069); Repair Chain Reaction (European Patent Publication No. 439,182 A2), 3SR (Kwoh et al 1989, *Proc. Natl. Acad. Sci. USA* 86:1173–1177; Guatelli et al 1990, *Proc. Natl. Acad. Sci. USA* 87:1874–1878; PCT Patent Publication No. WO 92/0880A), and NASBA (U.S. Pat. No. 5,130,238). All of the above references are incorporated herein by reference. This invention is not limited to any particular amplification system. As other systems are developed, those systems may benefit by practice of this invention. A recent survey of amplification systems was published in Abramson and Myers, 1993, *Current Opinion in Biotechnology* 4:41–47, incorporated herein by reference.

Sample preparation methods suitable for each amplification reaction are described in the art (see, for example, Sambrook et al., supra, and the references describing the amplification methods cited above). Simple and rapid methods of preparing samples for the PCR amplification of target sequences are described in Higuchi, 1989, in *PCR Technology* (Erlich ed., Stockton Press, New York), and in *PCR Protocols,* Chapters 18–20 (Innis et al., ed., Academic Press, 1990), both incorporated herein by reference. One of skill in the art will be able to select and empirically optimize a suitable protocol.

Methods for the detection of amplified products have been described extensively in the literature. Standard methods include analysis by gel electrophoresis or by hybridization with oligonucleotide probes. The detection of hybrids formed between probes and amplified nucleic acid can be carried out in variety of formats, including the dot-blot assay format and the reverse dot-blot assay format. (See Saiki et al, 1986, *Nature* 324:163–166; Saiki et al., 1989, *Proc. Natl. Acad. Sci. USA* 86:6230; PCT Patent Publication No. 89/11548; U.S. Pat. Nos. 5,008,182, and 5,176,775; PCR Protocols: A Guide to Methods and Applications (ed. Innis et al., Academic Press, San Diego, Calif.):337–347; each incorporated herein by reference. Reverse dot-blot methods using microwell plates are described in copending U.S. Ser. No. 141,355; U.S. Pat. No. 5,232,829; Loeffelholz et al., 1992, *J. Clin. Microbiol.* 30(11):2847–2851; Mulder et al., 1994, *J. Clin. Microbiol.* 32(2):292–300; and Jackson et al., 1991, *AIDS* 5:1463–1467, each incorporated herein by reference.

Another suitable assay method, referred to as a 5'-nuclease assay, is described in U.S. Pat. No. 5,210,015; and Holland et al, 1991, *Proc. Natl. Acad. Sci. USA* 88:7276–7280; both, incorporated herein by reference. In the 5'-nuclease assay, labeled probes are degraded concomitant with primer extension by the 5' to 3' exonuclease activity of the DNA polymerase, e.g., Taq DNA polymerase.

Detection of probe breakdown product indicates both that hybridization between probe and target DNA occurred and that the amplification reaction occurred. Copending U.S. Ser. Nos. 08/299,682, filed Sep. 1, 1994, and 08/347,657, filed Nov. 23, 1994, both incorporated herein by reference, describe improved methods for detecting the degradation of probe which occurs concomitant with amplification.

An alternative method for detecting the amplification of nucleic acid by monitoring the increase in the total amount of double-stranded DNA in the reaction mixture is described in Higuchi et al., 1992, *Bio/Technology* 10:413–417; Higuchi et al., 1993, *Bio/Technology* 11:1026–1030; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence. A problem in this method is that the synthesis of non-target sequence, i.e., non-specific amplification, results in an increase in fluorescence which interferes with the measurement of the increase in fluorescence resulting from the synthesis of target sequences. Thus, the methods of the present invention are particularly useful because they reduce non-specific amplification, thereby minimizing the increase in fluorescence resulting from the amplification of non-target sequences.

The present invention also relates to kits, multicontainer units comprising useful components for practicing the present method. A useful kit contains a reversibly-inactivated thermostable enzyme and one or more reagents for carrying out an amplification reaction, such as oligonucleotide primers, substrate nucleoside triphosphates, cofactors, and an appropriate buffer.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Polymerase Activity Assay

All measurements of DNA polymerase activity described in the Examples, below, were carried out using the following DNA polymerase activity assay. The assay is essentially as described in Lawyer et al., 1989, *J. Biol. Chem.* 264:6427–6437, and in the AmpliTaq® DNA polymerase product insert (Perkin Elmer, Norwalk, Conn.), both incorporated herein by reference.

One unit of enzyme activity is defined as the amount that will incorporate 10 nmoles of dNTP's into acid insoluble material per 30 minutes in a 10 minute incubation at 74° C. Because of the lability of the modified enzymes, activities were measured at 50° C. and normalized to a standard Taq DNA polymerase solution that had also been assayed at 74° C. Reactions were carried out in a 50 $\mu$l volume containing the following reagents:

25 mM TAPS (Tris-(hydroxymethyl)-methyl-amino-propanesulfonic acid, sodium salt), pH 9.3 (at room temperature);
50 mM KCl;
2 mM $MgCl_2$;
1 mM $\beta$-mercaptoethanol;
200 $\mu$M each of dATP, dGTP, and dTTP;
100 $\mu$M [$\alpha$-$^{32}$P]-dCTP (0.05–0.1 Ci/nmole);
activated salmon sperm DNA.

EXAMPLE 2

Citraconylation of Taq DNA Polymerase

This example describes the modification of Taq DNA polymerase using citraconic anhydride. Measurements of the activity of the citraconylated Taq DNA polymerase which indicate the molar ratio of modifier to enzyme in the inactivation reaction required to obtain complete inactivation of the DNA polymerase activity are described in Example 3, below.

Taq DNA polymerase (AmpliTaq®, Perkin Elmer, Norwalk Conn.) was used at an initial concentration of 1.3 mg/ml. In the initial experiments, the Taq DNA polymerase was first dialyzed against 1000× sodium borate at pH 8.63. This step was found to not be critical and in later experiments, Taq DNA polymerase was used in a Tris buffer (50 mM Tris-HCl, 1 mM EDTA, 65 mM KCl, pH 7.5) directly without dialysis against sodium borate.

Citraconic anhydride (11.06M) is commercially available (Aldrich, Milwaukee, Wis.). A starting solution of citraconic anhydride was created by diluting 11.06M citraconic anhydride 100-fold in DMF (N,N dimethyl formamide).

For one set of modification reactions, a dilution series of the citraconic anhydride solution was created by repeated 2-fold dilutions in DMF. For each solution in the series, 4 $\mu$l of diluted citraconic anhydride solution were added to 400 $\mu$l Taq DNA polymerase solution (with sodium borate dialysis), resulting in solutions containing molar ratios of citraconic anhydride to Taq DNA polymerase of approximately 80/1, 40/1, 20/1, and 10/1. Solutions were incubated overnight at 4° C. to inactivate the Taq DNA polymerase. As used herein, an enzyme which has been modified in a reaction with an N-fold molar excess of modifier is referred to as an NX enzyme. Thus, the resulting citraconylated Taq DNA polymerases are referred to herein as 80×, 40×, 20×, and 10× Taq DNA polymerases.

Additional modification reactions were carried out using approximately 80×, 160×, and 240× molar ratios of citraconic anhydride to Taq DNA polymerase (without sodium borate dialysis). The 160× and 240× ratios were created by suitable adjustment of the starting dilution of the 11.06M citraconic anhydride in DMF (N,N dimethyl formamide). For example, for a final 160× ratio, 11.06M citraconic anhydride was diluted 1/50 in DMF, and 4 $\mu$l of the resulting citraconic anhydride starting solution were added to 400 $\mu$l Taq DNA polymerase solution. The resulting citraconylated Taq DNA polymerases are referred to herein as 240×, 160×, and 80× Taq DNA polymerases.

EXAMPLE 3

Inactivation and Heat Recovery of DNA Polymerase Activity using Citraconic Anhydride This example describes activity measurements of the citraconylated Taq DNA polymerases of Example 2 both before and after re-activation of citraconylated Taq DNA polymerase by heat incubation. The effect of pH on the amount of activity recovered following heat reactivation of the citraconylated Taq DNA polymerases was measured.

Samples of citraconylated Taq DNA polymerase were diluted 1/200 in a buffer consisting of 10 mM Tris-HCl, 100 mM KCl, 2 mM MgCl$_2$, 0.5% Tween 20, 0.5% NP-40, 16% glycerol. The buffer pH was 8.25 at room temperature. Diluted samples of citraconylated Taq DNA polymerase were incubated at 90° C. for 20 minutes or maintained at room temperature as a control. Following treatment, samples were diluted 1/5 in enzyme dilution buffer (25 mM Tris-HCl, 50 mM KCl, 1 mM β-mercaptoethanol, 0.5% Tween 20, 0.5% NP-40, 0.1% gelatin) and the activity was assayed as described in Example 1. The DNA polymerase activities following treatment are shown below. The molar ratio refers to the molar ratio of citraconic anhydride to Taq DNA polymerase used in the modification reaction. Each of the activities is the average two activities measured from duplicate samples.

|  | Activity (% of control) | |
| --- | --- | --- |
| molar ratio | unheated | 90° C. incubation |
| Control | 100 | |
| 80X | 0 | 16 |
| 40X | 0 | 28 |
| 20X | 3.7 | 38 |
| 10X | 38 | 63 |

Complete inactivation of Taq DNA polymerase was obtained using greater than 20-fold molar excesses of citraconic anhydride. Following incubation of the completely inactivated Taq DNA polymerase at 90° C. for 20 minutes, a minimum of 16% of the activity was recovered.

Although more enzyme activity was recovered using the 40× citraconylated Taq DNA polymerase than using the 80× citraconylated Taq DNA polymerase, it may be more practical to use the 80× (or higher) citraconylated Taq DNA polymerase in a commercial kit to allow greater manufacturing tolerances.

Similar experiments were carried out using a buffer adjusted to pH 7.75 at room temperature. The results are shown below.

|  | Activity (% of control) | |
| --- | --- | --- |
| molar ratio | unheated | 90° C. incubation |
| Control | 100 | |
| 80X | 0 | 61 |
| 40X | 0 | 67 |
| 20X | 3.5 | 70 |
| 10X | 35 | 77 |

The amount of DNA polymerase activity recovered was greater at lower pH.

The activities of the 80× and 160× Taq DNA polymerases (without sodium borate dialysis) were measured before and after reactivation by heat incubation essentially as described above. The buffer pH used for the incubations was 8.0 at room temperature. The results are shown below. Each of the activities is the average two activities measured from duplicate samples.

|  | Activity (% of control) | |
| --- | --- | --- |
| molar ratio | unheated | 90° C. incubation |
| Control | 100 | |
| 160X | 0 | 19 |
| 80X | 0 | 29 |

The effect of pH on reactivation can be seen further by comparing the activity recovered using the 80× Taq DNA polymerases from the three reactivations at different pH. The above data indicate enzyme activity is recovered even when a high molar excess of modifier is used in the modification reaction.

EXAMPLE 4

PCR Amplification using Citraconylated Taq DNA Polymerases

This example describes the use of the citraconylated Taq thermostable DNA polymerase described in Example 2 in PCR amplifications.

PCR Protocol

Amplifications were carried out using 1/20, 1/40, and 1/80 dilutions of the 240× modified Taq DNA polymerase described in Example 2. Dilutions were made in a buffer consisting of 20 mM Tris-HCl, pH 8.0 (at room temperature), 100 mM KCl, 0.1 mM EDTA (ethylenediaminetetraacetic acid), 1 mM DTT (dithiothreitol), 50% glycerol, 0.5% Tween 20, 0.5% Nonidet P40 (AmpliTaq® storage buffer, Perkin Elmer, Norwalk, Conn.). For comparison, amplifications also were carried out using 1/10, 1/20, 1/40, and 1/80 dilutions of unmodified Taq DNA polymerase.

A cloned HTLV-I genomic sequence was amplified using primers SK432 and SK111. The primer sequences are provided in U.S. Pat. No. 5,418,149, incorporated herein by reference. The PCR was carried out in a 100 μl reaction volume under the following reaction conditions.

Reaction Mixture:

30 copies of HTLV-I DNA template 10 mM Tris, pH 8.3

50 mM KCl 0.5 μM of each primer

200 μM dATP, dCTP, and dGTP

400 μM dUTP 0.5 μl of citraconylated Taq DNA polymerase solution 2.5 mM MgCl$_2$ 1 ng hpDNA 1 unit of UNG (Perkin Elmer, Norwalk, Conn.)

Thermal Cycling Profile:

| Pre-reaction incubation: | | (90° C. for 10 minutes) |
| --- | --- | --- |
| 2 Cycles | Denature | 98° C. for 1 minute |
|  | Anneal/extend | 60° C. for 2 minute |
| 38 Cycles | Denature | 94° C. for 1 minute |
|  | Anneal/extend | 60° C. for 1 minute |
| Final incubation: |  | 60° C. for 7 minutes |

The amplified products were analyzed by 4% agarose gel electrophoresis using a 1× TBE (0.089M Tris, 0.089M boric acid, 0.0025M disodium EDTA) running buffer. Electrophoresis was carried out at 100 volts for approximately 2 hours. Ethidium bromide (0.5 μg/ml) was added following electrophoresis to stain any DNA present. The gel was destained in 1× TBE and the ethidium bromide-stained bands of DNA were visualized using UV irradiation.

Results

Figure 2:
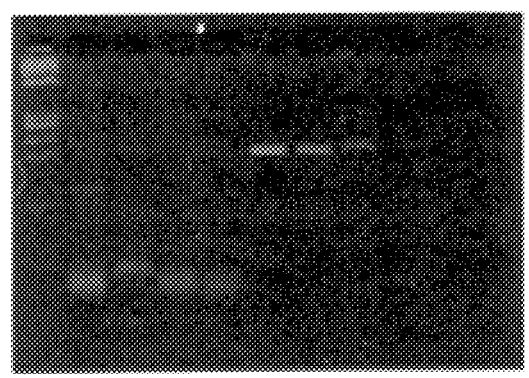
FIG. 2 shows the results of amplifications carried out using citraconylated Taq DNA polymerase as described in Example 4.

The results are presented in FIG. 2. The band corresponding to the amplified target sequence is indicated. Bands appearing on the gel other than the band which corresponds to the amplified target sequence correspond to the products generated by the non-specific amplification of non-target sequences. The effect of amplification using the citraconylated Taq DNA polymerase (labeled Taq, HS) can be seen by comparing the banding pattern and intensity within each of the lanes. Because the amplification of non-specific products competes with amplification of the target sequence, an increase in amplification of the target sequence further indicates the amount of the reduction in non-specific amplification. Hence, change in the relative amount of products within each lane best indicates the effect of a pre-reaction treatments on non-specific amplification.

Amplifications using unmodified Taq DNA polymerase resulted in predominantly non-specific amplification product. The use of citraconylated Taq DNA polymerase resulted in a significant increase in the intensity of the band corresponding to the amplified target sequence, and a significant decrease in the intensity of the bands corresponding to non-specific amplification products. The data indicate that PCR amplification using a reversibly-inactivated DNA polymerase significantly reduces non-specific amplification and significantly increases the amount of desired amplified target sequence.

EXAMPLE 5

Other Citraconylated Thermostable DNA Polymerases

This example described the citraconylation of several other thermostable DNA polymerases in addition to the Taq DNA polymerase described above. The following thermostable DNA polymerases were modified:

1) a thermostable DNA polymerase from *Thermus thermophilus* (rTth, Perkin Elmer, Norwalk, Conn.), as described in PCT/US/90/07639, incorporated herein by reference.

2) a mutant thermostable DNA polymerase from *Thermatoga maritima* (UlTma, Perkin Elmer, Norwalk, Conn.), as described in PCT/US/91/09294, incorporated herein by reference.

3) a mutant form of thermostable DNA polymerase from *Thermus aquaticus* which lacks 3' to 5' exonuclease, activity as described in PCT/US91/0703, incorporated herein by reference. This enzyme is referred to herein as Taq CS or AmpliTaq® CS.

For each of the above three DNA polymerases, an initial solution was prepared at an approximate concentration of 200 units/µl. For comparison, 1.3 mg/ml Taq DNA polymerase, as used in the previous examples, is approximately equivalent to 260 units/µl. Each of the DNA polymerases was modified essentially as described in Example 2, above. Ten µl of citraconic anhydride were diluted in 500 µl of DMF. Then, 10 µl of diluted citraconic anhydride were combined with 1000 µl of each of the enzyme solutions. The resulting solutions were incubated overnight at 4° C.

EXAMPLE 6

PCR Amplification using Citraconylated DNA Polymerases

This example describes the use of the citraconylated thermostable DNA polymerases described in Examples 2 and 5 in PCR amplifications.

PCR Protocol

Amplifications were carried out using dilutions of modified DNA polymerases. Dilutions were made in a buffer consisting of 20 mM Tris-HCl, pH 8.0 (at room temperature), 100 mM KCl, 0.1 mM EDTA (ethylenediaminetetraacetic acid), 1 mM DTT (dithiothreitol), 50% glycerol, 0.5% Tween 20, 0.5% Nonidet P40 (AmpliTaq® storage buffer, Perkin Elmer, Norwalk, Conn.).

An HIV-1 genomic sequence was amplified using primers SK145 and SK431 (Perkin Elmer, Norwalk, Conn.). The PCR was carried out in a 100 µl reaction volume under the following reaction conditions.

Reaction Mixture:
  100 copies of HIV-1 DNA template
  10 mM Tris, pH 8.3
  50 mM KCl
  0.5 µM of each primer
  200 µM dATP, dCTP, and dGTP
  400 µM dUTP
  0.5 µl of DNA polymerase solution
  2.5 mM $MgCl_2$
  1 ng hpDNA
  1 unit of UNG (Perkin Elmer, Norwalk, Conn.)
Thermal Cycling Profile:

| | | |
|---|---|---|
| Pre-reaction incubation: | (95° C. for 12 minutes) | |
| 38 Cycles | Denature | 94° C. for 1 minute |
| | Anneal/extend | 60° C. for 1 minute |
| Final incubation: | | 60° C. for 7 minutes |

The pre-reaction incubation step also serves as the initial denaturation step. An initial denaturation step is routinely used in a typical amplification reaction to insure complete denaturation of the double-stranded target. Each cycle of the PCR begins with a denaturation step of 94° C. for 1 minute. Thus, immediately following the initial pre-reaction incubation carried out at 95° C. for 12 minutes, the reaction mixture is incubated at 94° C. for 1 minute during the denaturation step of the first cycle.

The amplified products were analyzed by agarose gel electrophoresis (100 ml of 3% NuSieve and 0.5% SeaChem) using a 1× TBE (0.089M Tris, 0.089M boric acid, 0.0025M disodium EDTA) running buffer. Electrophoresis was carried out at 100 volts for approximately 1 hour. Ethidium bromide (0.5 µg/ml) was added following electrophoresis to stain any DNA present. The gel was destained in TBE and the ethidium bromide-stained bands of DNA were visualized using UV irradiation.

Amplifications using Citraconylated DNA Polymerases

Dilutions (1/10, 1/20, 1/40, and 1/80) of the citraconylated DNA polymerases described in Example 5 and the 240× citriconylated Taq DNA polymerase described in Example 2 were used in amplifications of HIV-1 nucleic acid and the amplified products were anaylzed by agarose gel electrophoresis. For comparison, amplifications were carried out using dilutions of unmodified Taq DNA polymerase.

Figure 3:
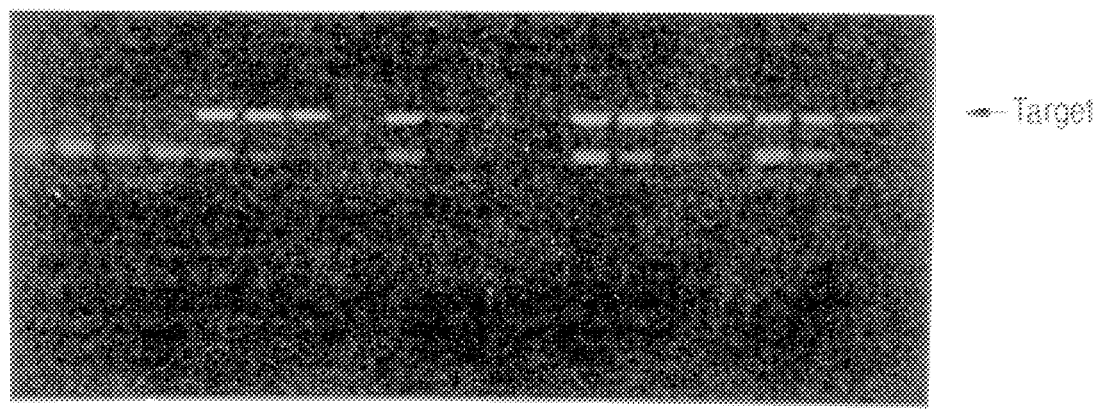
FIG. 3 shows the results of amplifications carried out using citraconylated DNA polymerases as described in Example 6.

The results are presented in FIG. 3. The band corresponding to the amplified target sequence is indicated. Bands appearing on the gel other than the band which corresponds to the amplified target sequence correspond to the products generated by the non-specific amplification of non-target sequences. The effect of amplification using a citraconylated DNA polymerase can be seen by comparing the banding pattern and intensity within each of the lanes. Because the amplification of non-specific products competes with amplification of the target sequence, an increase in amplification of the target sequence further indicates the amount of the reduction in non-specific amplification. Hence, change in the relative amount of products within each lane best indicates the effect of a pre-reaction treatments on non-specific amplification.

Amplifications using unmodified Taq DNA polymerase resulted in predominantly non-specific amplification product for dilution levels of enzyme. The use of citraconylated Taq DNA polymerase resulted in a intense band corresponding to the amplified target sequence for all but the 1/80 dilution, and a significant decrease in the intensity of the band corresponding to non-specific amplification products. The data indicate that PCR amplification using a reversibly-inactivated DNA polymerase significantly reduces non-specific amplification and significantly increases the amount of desired amplified target sequence.

The use of citraconylated UlTma, Taq CS, and rTth DNA polymerases also resulted in a greater production of specific amplification product than seen in amplifications using unmodified Taq DNA polymerase, along with the concomitant reduction in the amount of non-specific amplification product. The results demonstrate that the methods of the present invention are applicable to thermostable DNA polymerases in general.

It should be noted that, although the results demonstrate the functionality of the present invention, the results obtained using the citraconylated Taq, UlTma, Taq CS, and rTth DNA polymerases are not directly comparable because the modification conditions were not comparably optimized for each DNA polymerase. In particular, although each initial solution of DNA polymerase contained the same units/ml, the molarity of the solutions was not determined and, therefore, the molar excess of citraconic anhydride in each modification reaction was not determined. One of skill will recognize that optimum modification conditions can be determined empirically using the protocols described herein.

EXAMPLE 7

Cis-Aconityled DNA Polymerase

This example describes the modification of Taq DNA polymerase using cis-aconitic anhydride.

Modification using cis-aconitic anhydride was carried out essentially as described in Example 2, differing mainly because cis-aconitic anhydride is sold as a powder and not as a liquid. Taq DNA polymerase (AmpliTaq®, Perkin Elmer, Norwalk Conn.) in a Tris buffer (50 mM Tris-HCl, 1 mM EDTA, 68 mM HCl, pH 7.5) was used at a starting concentration of 1.3 mg/ml. A starting solution of cis-aconitic anhydride (Aldrich, Milwaukee, Wis.) was created by dissolving 20 mg of cis-aconitic anhydride in 1 ml 100% EtOH.

Either 10 or 20 µl of cis-aconitic anhydride solution were added to 1000 µl Taq DNA polymerase solution, resulting in solutions containing molar ratios of cis-aconitic anhydride to Taq DNA polymerase of approximately 90 and 180. Solutions were incubated overnight at 4° C. to inactivate the Taq DNA polymerase.

Comparisons of amplifications using the cis-aconitylated Taq DNA polymerase and amplifications using citraconylated Taq DNA polymerase are described below.

EXAMPLE 8

Inactivation and Heat Recovery of DNA Polymerase Activity using Cis-Aconitic Anhydride The activities of the 90× and 180× cis-aconitylated Taq DNA polymerases prepared in Example 7 were measured before and after reactivation by heat incubation essentially as described in Example 3, above. The buffer pH during the incubations was 8.0. The results are shown below. Each of the activities is the average two activities measured from duplicate samples.

| | Activity (% of control) | |
|---|---|---|
| molar ratio | unheated | 90° C. incubation |
| Control | 100 | |
| 180X | 0 | 50 |
| 90X | 3 | 118 |

A comparison of the results with those of Example 3 indicate that cis-aconitylation is more easily reversed than citraconylation. A higher molar excess of cis-aconitic anhydride is needed to completely inactivate the DNA polymerase and more activity is recovered following a high temperature incubation. The reason for the activity measurement of greater than 100% following modification with a 90-fold molar excess of cis-aconitic anhydride followed by heat reactivation is unknown, but may be caused by imprecision in the activity assay or may reflect an actual modification of the DNA polymerase.

EXAMPLE 9

Effect of Pre-Reaction Incubation Time

This example describes the effect of the pre-reaction incubation time on the amount of product obtained.

Amplifications were carried out using the citraconylated and cis-aconitylated Taq DNA polymerases prepared as described above. For each set of amplification conditions, Taq DNA polymerases modified using a 80-fold and a 160-fold molar excess of citaconic anhydride, and a 90-fold and a 180-fold molar excess of cis-aconitic anhydride were used. Amplifications were carried out using the HIV-1 model system described in Example 6, above, except that the initial pre-reaction incubation was varied. For each enzyme preparation, amplifications were carried out using pre-reaction incubations of 12, 6, 3, and 0 minutes.

As noted above, the pre-reaction incubation step also serves as the initial denaturation step. Each cycle of a PCR begins with a denaturation step. Immediately following the initial pre-reaction incubation carried out at 95° C. for 12, 6, 3, or 0 minutes, each reaction mixture is incubated at 94° C. for 1 minute during the denaturation step of the first cycle. Thus, even when no pre-reaction incubation was used, enzyme activity is recovered during the denaturation step of the initial cycles.

Figure 4:
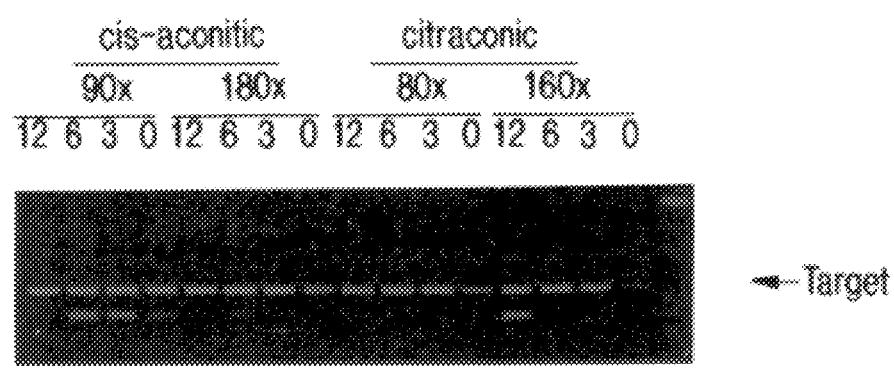
FIG. 4 shows the results of varying the pre-reaction incubation time in amplifications carried out using citraconylated and cis-aconitylated DNA polymerases as described in Example 9.

The amplification products were analyzed by agarose gel electrophoresis. The results are presented in FIG. 4. The band corresponding to the amplified target sequence is indicated. Bands appearing on the gel other than the band which corresponds to the amplified target sequence correspond to the products generated by the non-specific amplification of non-target sequences.

The results show that, using cis-aconitylated DNA polymerase, all pre-reaction incubation times resulted in a strong band corresponding to amplified product. Amplifications carried out without a pre-reaction incubation resulted in nearly as much product as the amplifications using an extended pre-reaction incubations.

In contrast, the results show that, using citraconylated DNA polymerase, a pre-reaction incubation of at least 3 minutes was required to obtain the maximum amount of amplified product. Amplifications carried out without a pre-reaction incubation resulted in significantly less amplified product. The results indicate that activity of cis-aconitylated DNA polymerases is recovered more rapidly than for citraconylated DNA polymerases.

EXAMPLE 10

Effect of Cycle Number

This example describes the effect of the increasing the amplification cycle number to compensate for a short pre-reaction incubation time.

Amplifications were carried out using the Taq DNA polymerases modified using a 80-fold and a 160-fold molar excess of citraconic anhydride, and a 90-fold and a 180-fold molar excess of cis-aconitic anhydride. The Amplifications were carried out essentially as described above using the HIV-1 model system described in Example 6, except that the initial pre-reaction incubation and cycle numbers were varied. For each enzyme preparation, amplifications were carried out using the following conditions:

| pre-reaction incubation | amplification cycles |
|---|---|
| 12 minute, 80C | 60 |
| 0 | 60 |
| 0 | 48 |
| 0 | 43 |
| 0 | 39 |

Figure 5:
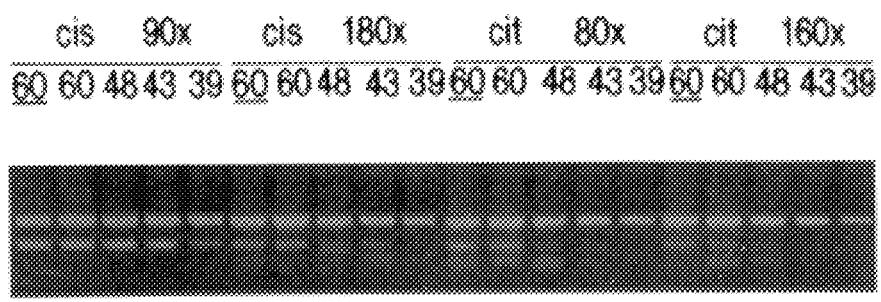
FIG. 5 shows the results of varying the amplification cycle number in amplifications carried out using citraconylated and cis-aconitylated DNA polymerases as described in Example 10.

The amplification products were analyzed by agarose gel electrophoresis. The results are presented in FIG. 5. The results show that increasing the amplification cycle number can compensate for the loss of amplification efficiency resulting from the incomplete reactivation of DNA polymerase activity when no pre-reaction incubation is used.

For each DNA polymerase, increasing the amplification cycle number resulted in an increase in amplified product. The effect was smallest when using cis-aconitylated Taq DNA polymerase, which was shown in Example 9 to require little if any pre-reaction incubation.

We claim:

1. A method for the amplification of a target nucleic acid contained in a sample comprising the steps of:
   (a) contacting said sample with an amplification reaction mixture containing a primer complementary to said target nucleic acid and a modified thermostable enzyme, wherein said modified thermostable enzyme is produced by a reaction of a mixture of a thermostable enzyme which catalyzes a primer extension reaction and a modifier reagent, wherein said reaction results in a covalent chemical modification of said enzyme which results in essentially complete inactivation of enzyme activity, wherein incubation of said modified enzyme in an aqueous buffer at alkaline pH at a temperature less than about 25° C. results in no significant increase in enzyme activity in less than about 20 minutes, and wherein incubation of said modified enzyme in an aqueous buffer, formulated to about pH 8–9 at 25° C., at a temperature greater than about 50° C. results in at least a two-fold increase in enzyme activity in less than about 20 minutes; and
   (b) incubating the resulting mixture of step (a) at a temperature which is greater than about 50° C. for a time sufficient to reactivate said enzyme and allow formation of primer extension products.

2. A method for the amplification of a target nucleic acid contained in a sample comprising the steps of:
   (a) contacting said sample with an amplification reaction mixture containing a primer complementary to said target nucleic acid and a modified thermostable enzyme, wherein said modified thermostable enzyme is produced by a reaction of a mixture of a thermostable ligase and a modifier reagent, wherein said reaction is carried out at alkaline pH at a temperature which is less than about 25° C., wherein said reagent is a dicarboxylic acid anyhydride of the general formula:

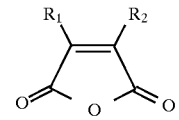

where $R_1$ and $R_2$ are hydrogen or organic radicals, which may be linked, or of the general formula:

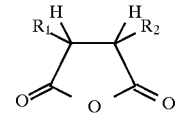

where $R_1$ and $R_2$ are organic radicals, which may be linked, and the hydrogen are cis and wherein said reaction results in essentially complete inactivation of enzyme activity; and
   (b) incubating the resulting mixture of step (a) at a temperature which is greater than about 50° C. for a time sufficient to reactivate said enzyme and allow formation of primer extension products.

3. The method of claim 2, wherein said modifier reagent is selected from the group consisting of maleic anhydride; exo-cis-3,6-endoxo-$\Delta^4$-tetrahydropthalic anhydride; citraconic anhydride; 3,4,5,6-tetrahydrophthalic anhydride; cis-aconitic anhydride; and 2,3-dimethylmaleic anhydride.

4. The method of claim 3, wherein said modifier reagent is citraconic anhydride or cis-aconitic anhydride.

5. The method of claim 4, wherein said wherein said modified thermostable enzyme is produced by a reaction of a mixture of said thermostable ligase and a greater than 20-fold molar excess of said compound.

6. A modified thermostable enzyme, wherein said modified thermostable enzyme is produced by a reaction of a mixture of a thermostable enzyme which catalyzes a primer extension reaction and a modifier reagent, wherein said reaction results in a covalent chemical modification of said enzyme which results in essentially complete inactivation of enzyme activity, wherein incubation of said modified enzyme in an aqueous buffer at alkaline pH at a temperature less than about 25° C. results in no significant increase in enzyme activity in less than about 20 minutes, and wherein incubation of said modified enzyme in an aqueous buffer, formulated to about pH 8–9 at 25° C., at a temperature greater than about 50° C. results in at least a two-fold increase in enzyme activity in less than about 20 minutes.

7. A modified thermostable enzyme, wherein said modified thermostable enzyme is produced by a reaction of a mixture of a thermostable ligase and a modifier reagent, wherein said reaction is carried out at alkaline pH at a temperature which is less than about 25° C., wherein said reagent is a dicarboxylic acid anyhydride of the general formula:

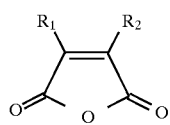

where $R_1$ and $R_2$ are hydrogen or organic radicals, which may be linked, or of the general formula:

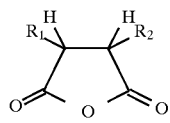

where $R_1$ and $R_2$ are organic radicals, which may be linked, and the hydrogen are cis and wherein said reaction results in essentially complete inactivation of enzyme activity.

8. The modified thermostable enzyme of claim 7, wherein said modifier reagent is selected from the group consisting of maleic anhydride; exo-cis-3,6-endoxo-$\Delta^4$-tetrahydropthalic anhydride; citraconic anhydride; 3,4,5,6-tetrahydrophthalic anhydride; cis-aconitic anhydride; and 2,3-dimethylmaleic anhydride.

9. The modified thermostable enzyme of claim 8, wherein said modifier reagent is citraconic anhydride or cis-aconitic anhydride.

10. The modified thermostable enzyme of claim 9, wherein said wherein said modified thermostable enzyme is produced by a reaction of a mixture of said thermostable ligase and a greater than 20-fold molar excess of said compound.

11. A kit for carrying out a polymerase chain reaction comprising a modified thermostable enzyme of claim 8.

12. A kit for carrying out a polymerase chain reaction comprising a modified thermostable enzyme of claim 9.

13. A kit for carrying out a polymerase chain reaction comprising a modified thermostable enzyme of claim 10.

* * * * *